(12) United States Patent
Wang et al.

(10) Patent No.: US 9,265,478 B2
(45) Date of Patent: Feb. 23, 2016

(54) WIRELESS ELECTRONIC STETHOSCOPE

(71) Applicant: MedicusTek Inc., Taipei (TW)

(72) Inventors: Chih-Hung Jason Wang, Taipei (TW);
Jonathan Lun-Chang Tong, Taipei
(TW); Chia-Ming Hsu, Taipei (TW);
Chung-Chih Lin, Taipei (TW); **Chun
Lin, Taipei (TW); Ling-Hsuan Liu**,
Taipei (TW); Mark Daniel Anderson,
Taipei (TW)

(73) Assignee: MedicusTek Inc., Taipei (TW)

( * ) Notice: Subject to any disclaimer, the term of this
patent is extended or adjusted under 35
U.S.C. 154(b) by 69 days.

(21) Appl. No.: 14/210,472

(22) Filed: Mar. 14, 2014

(65) Prior Publication Data

US 2014/0270218 A1 Sep. 18, 2014

Related U.S. Application Data

(60) Provisional application No. 61/786,665, filed on Mar. 15, 2013.

(51) Int. Cl.
*H04R 23/00* (2006.01)
*A61B 7/04* (2006.01)

(52) U.S. Cl.
CPC .......... *A61B 7/04* (2013.01); *A61B 2560/0418* (2013.01)

(58) Field of Classification Search
CPC ... H04R 23/00; A61B 7/04; A61B 2560/0418
USPC ............ 361/679.54; 370/331; 381/67; 600/1,
600/528, 586; 434/322; 607/57
See application file for complete search history.

(56) References Cited

U.S. PATENT DOCUMENTS

| 4,878,501 | A * | 11/1989 | Shue ............................ 600/528 |
| 5,027,825 | A * | 7/1991 | Phelps, Sr. ............ A61B 5/0002 600/528 |
| 5,855,483 | A * | 1/1999 | Collins ............... A63F 3/00643 434/307 R |
| 6,544,198 | B2 * | 4/2003 | Chong et al. .................. 600/586 |
| 7,346,174 | B1 * | 3/2008 | Smith ..................... A61B 7/026 181/131 |
| 7,969,730 | B1 * | 6/2011 | Doherty et al. .......... 361/679.54 |
| 8,548,174 | B2 * | 10/2013 | Dufresne ................. A61B 7/04 381/67 |
| 8,594,339 | B2 * | 11/2013 | Dufresne ............... A61B 5/061 181/131 |
| 8,956,305 | B2 * | 2/2015 | Trice ............................ 600/528 |
| 2006/0095090 | A1 * | 5/2006 | De Ridder ........... A61N 1/0529 607/57 |
| 2006/0221902 | A1 * | 10/2006 | Chen et al. ..................... 370/331 |
| 2006/0227979 | A1 * | 10/2006 | Chen .............................. 381/67 |
| 2014/0018779 | A1 * | 1/2014 | Worrell et al. ..................... 606/1 |
| 2014/0270218 | A1 * | 9/2014 | Wang et al. ..................... 381/67 |
| 2015/0148707 | A1 * | 5/2015 | Bedingham .............. A61B 7/04 600/586 |

* cited by examiner

*Primary Examiner* — Gerald Gauthier
(74) *Attorney, Agent, or Firm* — Osha Liang LLP

(57) ABSTRACT

A wireless electronic stethoscope device is disclosed. The wireless electronic stethoscope device includes a pen-shaped main body; a sensor module for data collection; a processor module to coordinate operation of electronic stethoscope modules; a wireless communication module to transmit and receive digital and analog data; a power module including a battery for storing energy; a control module to communicate information and receive operational commands.

25 Claims, 13 Drawing Sheets

WIRELESS ELECTRONIC STETHOSCOPE

RELATED APPLICATIONS

This application claims the priority benefit of U.S. Provisional Application Ser. No. 61/786,665, filed Mar. 15, 2013, the full disclosures of which are incorporated herein by reference.

BACKGROUND

1. Field of Invention

The present disclosure relates to electronic devices, and more particularly, to medical diagnostic devices for auscultation.

2. Description of Related Art

Stethoscopes have long been used for auscultation, which is the process of listening to the internal sounds of the human body, such as those of the heart and lungs. The application of new technologies to the design of stethoscopes can provide healthcare personnel with instruments that support improved patient outcomes. The capture of body sounds and subsequent translation to electrical signals enables amplification, filtering, and other signal processing to improve the diagnostic quality of audio signals presented to a clinician. Reduction of the electrical signals representing body sounds to digital form further facilitates the application of a large complement of widespread computer-related technology for data storage, transmission, and processing. Examples of this application include incorporation of recorded body sounds into patient electronic medical records and replay of body sounds for analysis by one or more clinicians. Moreover, when digital audio files are transmitted over electronic data networks additional benefits may be realized. These include diagnosis at a distance, collaboration by physically distant healthcare personnel, and the use of remotely hosted computational healthcare services including automated expert-system diagnosis and population-level analysis of data from many patients.

SUMMARY

The following presents a simplified summary of the disclosure in order to provide a basic understanding to the reader. This summary is not an extensive overview of the disclosure and it does not delineate the scope of the present invention. Its sole purpose is to present some concepts disclosed herein in a simplified form as a prelude to the more detailed description that is presented later.

According to one embodiment of the present disclosure, a wireless electronic stethoscope device includes a pen-shaped main body; a sensor module for data collection; a processor module to coordinate operation of electronic stethoscope modules; a wireless communication module to transmit and receive digital and analog data; a power module including a battery for storing energy; and a control module to communicate information and receive operational commands.

Many of the attendant features will be more readily appreciated, as the same becomes better understood by reference to the following detailed description considered in connection with the accompanying drawings.

BRIEF DESCRIPTION OF THE DRAWINGS

The present description will be better understood from the following detailed description read in light of the accompanying drawing, wherein.

DETAILED DESCRIPTION

Figure 1A:
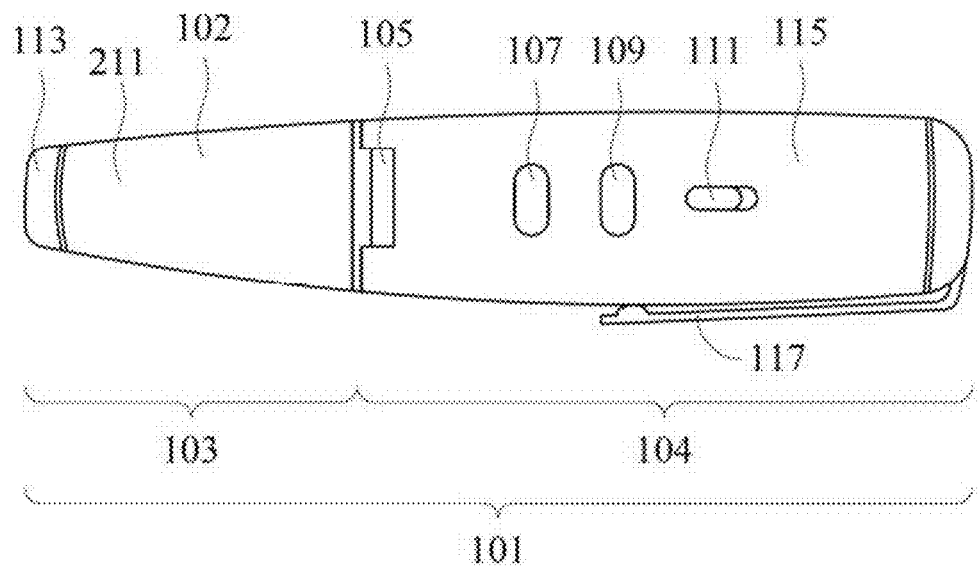
FIG. 1A is a right side orthogonal view of a wireless pen-shaped electronic stethoscope showing the pen-shaped main body and several external user interface controls of the main body control module according to one embodiment of the present disclosure.

In the following detailed description, for purposes of explanation, numerous specific details are set forth in order to attain a thorough understanding of the disclosed embodiments. In accordance with common practice, the various described features/elements are not drawn to scale but instead are drawn to best illustrate specific features/elements relevant to the present invention. Also, like reference numerals and designations in the various drawings are used to indicate like elements/parts. Moreover, well-known structures and devices are schematically shown in order to simplify the drawings and to avoid unnecessary limitation to the claimed invention.

The present invention relates to a wireless electronic stethoscope. The description discloses physical structure, functional component modules, processes of operation, and methods of use of the wireless electronic stethoscope.

In the following detailed description, for purposes of explanation, numerous specific details are set forth in order to attain a thorough understanding of the disclosed embodiments. It will be apparent, however, that one or more embodiments may be practiced without these specific details. In other instances, well-known structures and devices are schematically shown in order to simplify the drawing.

As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "in" includes "in" and "on" unless the context clearly dictates otherwise.

Physical Structure of the Wireless Electronic Stethoscope

The wireless electronic stethoscope (stethoscope) is designed to have a physical structure and an arrangement of user interface controls that together facilitate hand-held operation by a clinician. FIGS. 1A through 1K present one embodiment of the electronic stethoscope device. In FIG. 1A, a right side orthogonal view of pen-shaped main body 101 shows both the main body upper piece 104 and the main body lower piece 103, which includes the sensor module. The enclosing lower exterior case 102 and upper exterior case 115 are manufactured to produce a stethoscope of pen-shaped design that is amenable to hand-held operation by a clinician. The removable protective cap 113, when attached to the stethoscope as illustrated in FIG. 1A, is contiguous with the distal end of the main body lower piece 103 covering a microphone disposed at the bottom tip of stethoscope 101. The removable protective cap 113 is located at the first terminal of the pen-shaped main body 101 for protecting the sensor module 211. The main body control module provides user interface controls that include button 105 to start and stop recording of audio data collected by the microphone in the main body audio module, power switch 111 to physically enable and disable transfer of electrical energy from the main body power module to other modules, and buttons 107 and 109 that decrease and increase, respectively, the signal strength of output from the main body audio module via the audio output jack. The sensor module 211 is located in the pen-shaped main body 101 and is close to a first terminal of the pen-shaped main body 101, and the pen-shaped main body 101 has a clip 117, one end of the clip 117 is attached to a second terminal of the pen-shaped main body 101, a cross-sectional area of the second terminal of the pen-shaped main body 101 is larger than the first terminal of the pen-shaped main body 101. Specifically, the clip 117 is located adjacent to the backside of the stethoscope. It is attached to the plastic housing at the top of the stethoscope, and is constructed of a material sufficiently flexible so that the distal tip nearest the bottom of the stethoscope lifts from a resting position on the back of the stethoscope allowing insertion of paper or fabric, such as may form a shirt or coat pocket.

Figure 1B:
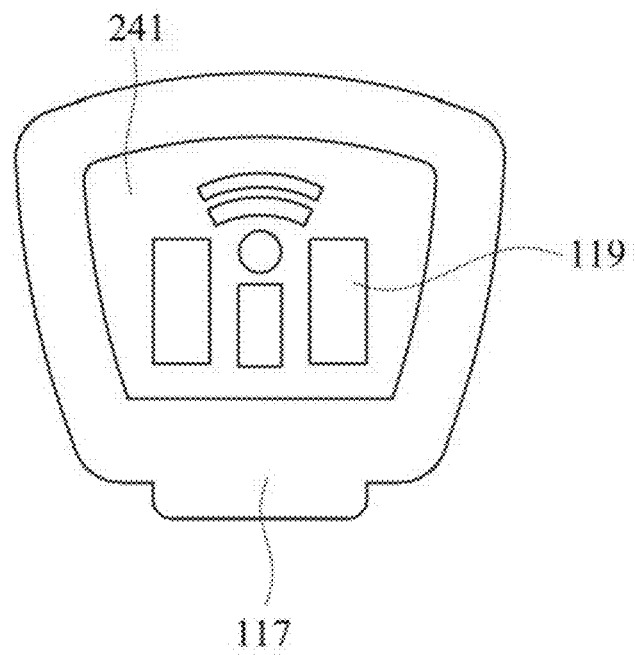
FIG. 1B is a top orthogonal view of the stethoscope of FIG. 1A.

FIG. 1B shows an orthogonal view of the top of pen-shaped main body 101 including the proximal end of clip 117 attached to the upper stethoscope housing. The second terminal of the pen-shaped main body 101 has an end cap 119 that is made of elastic material, and a power module 241 including a battery located adjacent to the end cap 119. The end cap 119 may be used for display of a brand logo and, in one embodiment, as a cover for a compartment of appropriate size to hold one or more removable batteries supplying electrical energy to the power module 241. In use, the power module 241 has a power saving mode.

Figure 1C:
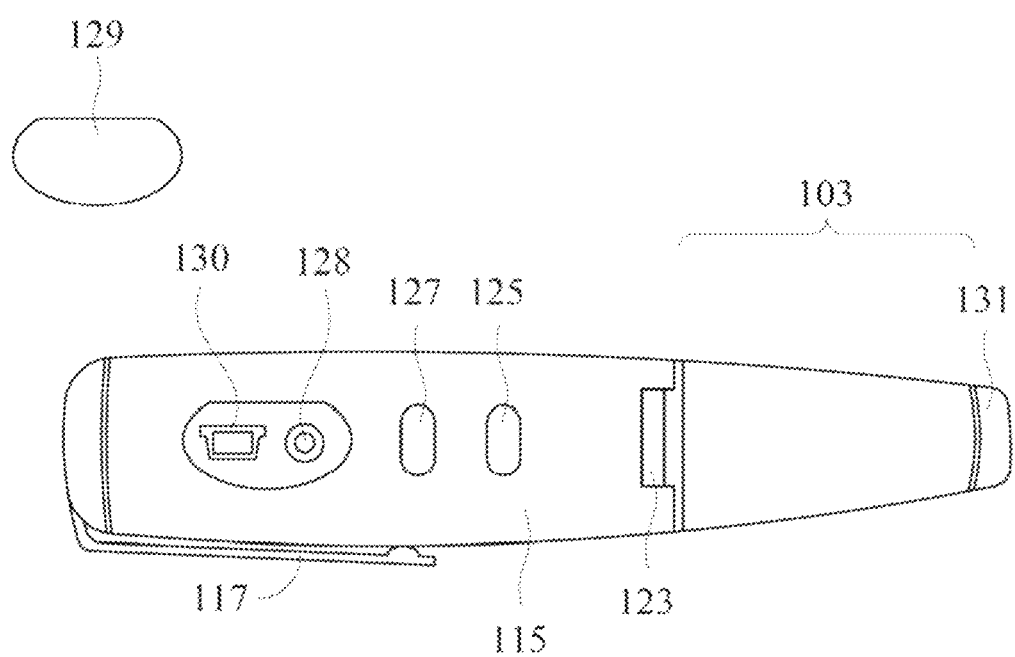
FIG. 1C is a left side orthogonal view of the stethoscope of FIG. 1A showing several external user interface controls of the main body control module, the exterior audio output jack of the main body audio module, the exterior data transfer jack of the main body control module, and the detached protective cover for both audio output and data transfer jacks.

FIG. 1C shows a left side orthogonal view of stethoscope 101. Exterior mode selection button 123 of the main body control module selects the audio filtering mode utilized by the digital signal processor in the main body processor module. Exterior interface controls of the main body control module include buttons 125 and 127 that start and stop, respectively, the play, or audio output transmission, of sounds previously recorded by the sensor module. The exterior audio port, or jack, 128 of the main body audio module accepts a standard 3.5 millimeter "mini" stereo audio plug for output transmission of electrical audio signals. Exterior data transfer port, or jack, 130 accepts a standard Universal Serial Bus (USB) Mini-B plug for transmission of audio data consistent with an industry-standard USB signaling and data transfer protocol for communication with the main body processor module. FIG. 1C shows removable protective cover 129 in a position detached from the upper stethoscope housing 115. When attached, cover 129 is disposed on the side of the upper stethoscope housing 115 covering the recessed compartment containing ports 128 and 130. FIG. 1C also includes the side view of exterior housing 131 around the perimeter of the sensor module at the bottom of the stethoscope. In this figure protective cap 113 is not attached.

Figure 1D:
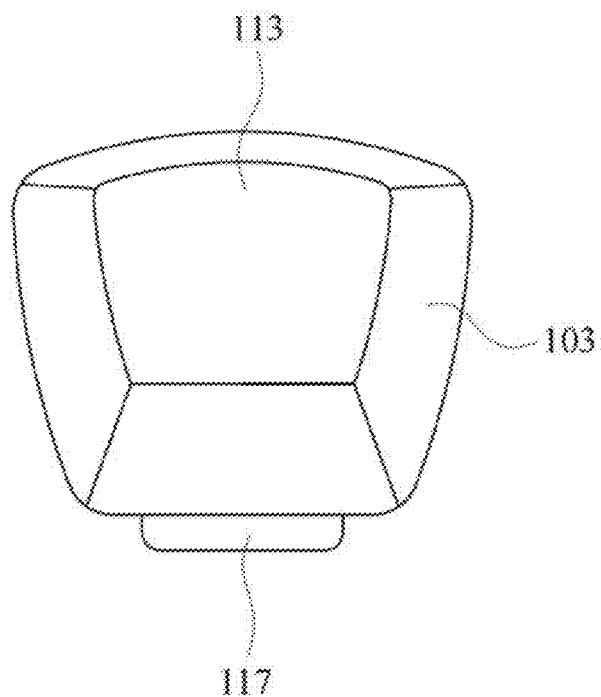
FIG. 1D is a bottom orthogonal view of the stethoscope of FIG. 1A showing the cover protecting the external microphone of the stethoscope sensor module.
Figure 1E:
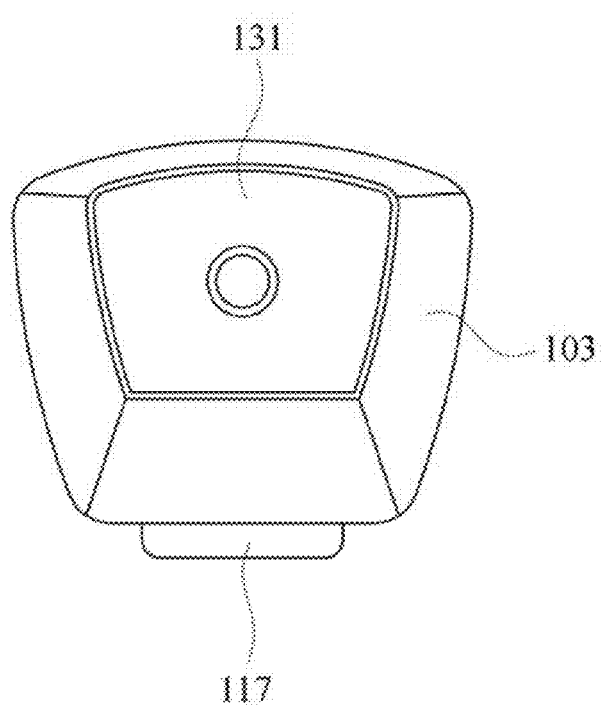
FIG. 1E is a bottom orthogonal view of the stethoscope of FIG. 1A showing the uncovered external microphone of the stethoscope sensor module.

FIGS. 1D and 1E show orthogonal views of the bottom of stethoscope 101. In FIG. 1D protective cap 113 is attached to main body lower piece 103 covering exterior housing 131 surrounding the sensor module. The protruding tab at back side of the protective cap, contiguous with the back surface of stethoscope 101, facilitates removal of the cap from exterior housing 131. FIG. 1E shows a bottom view of the exposed, uncovered, exterior housing 131, which has a centrally-concave bottom surface contour centered about the recessed microphone. The first terminal of the pen-shaped main body 101 has a centrally concave bottom surface, and the sensor module 221 has a microphone positioned in a center of the centrally concave bottom surface. This contouring may function to both protect the microphone and direct sound to the microphone receiver surface.

Figure 1F:
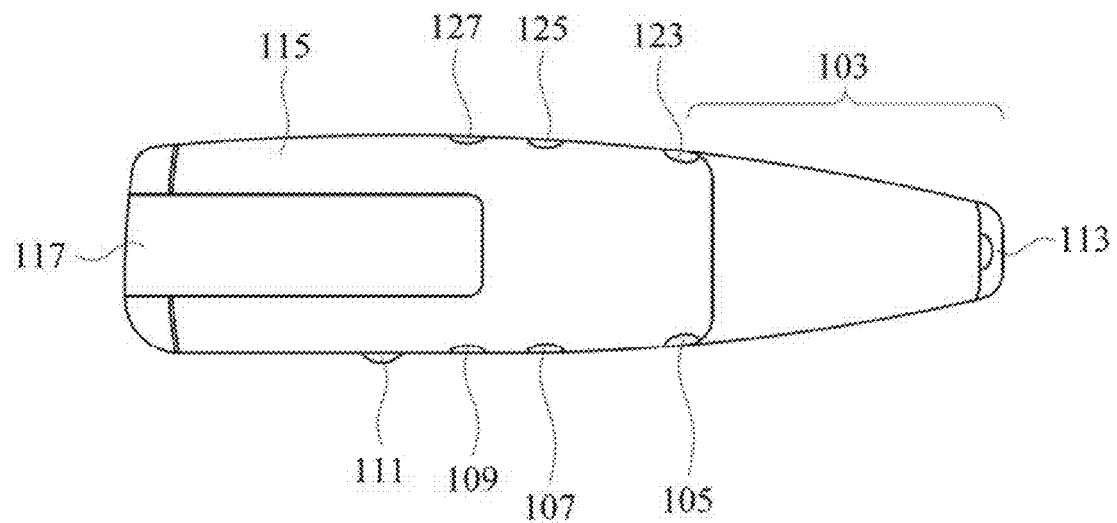
FIG. 1F is a back orthogonal view of the stethoscope of FIG. 1A showing the clip on the pen-shaped main body.

FIG. 1F shows an orthogonal view of the back of stethoscope 101 that displays the back surface of clip 117 as well as side views of user interface control buttons and switches disposed on the right and left sides of the stethoscope. The back of protective cap 113 is visible with the cap attached to the stethoscope.

Figure 1G:
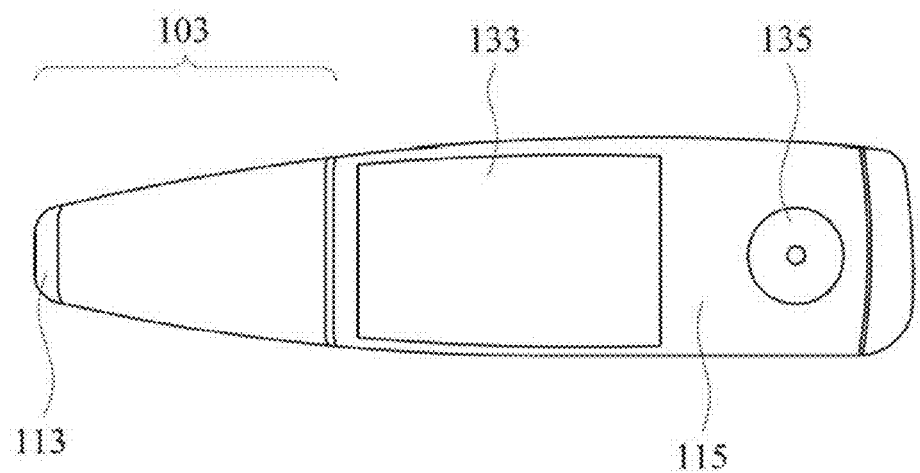
FIG. 1G is a front orthogonal view of the stethoscope of FIG. 1A showing the exterior display screen and an external button of the main body control module.

FIG. 1G shows an orthogonal view of the front of stethoscope 101 including two exterior user interface components of the main body control module, touch display screen 133 and control button 135. The touch display screen 133 is disposed in a side of the pen-shaped main body 101, and configured to display stethoscope status information that may includes info based on the audio data, input info, or a message received from a server. The touch display screen 133 communicates to the user stethoscope status information such as the current operating mode, the available recorded and stored audio data files, the status of the wireless transceiver in the stethoscope main body wireless communication module, and state of wireless connections with one or more external wireless receivers. Control button 135 enables the user to select the desired functionality from among the available set of functionalities programmed into the main body processor module, which may vary with different models of the stethoscope.

Figure 1H:
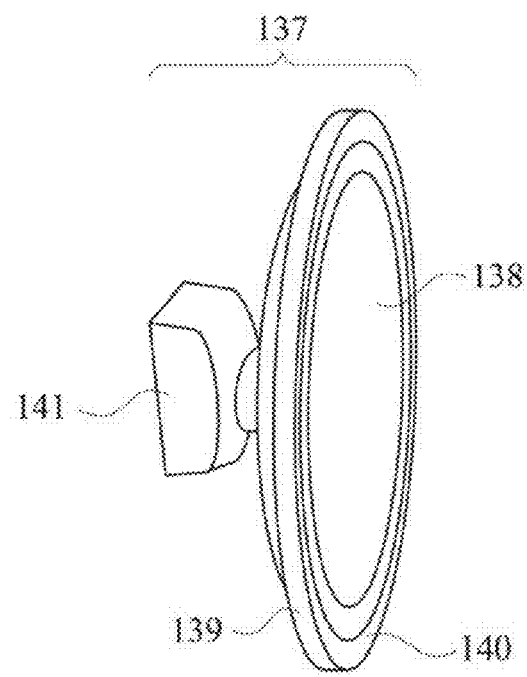
FIG. 1H is a side perspective view of the detachable bell module according to one embodiment of the present disclosure.

FIG. 1H shows a side perspective view of detachable bell module 137 that is located adjacent to the sensor module 211 when connecting the first terminal of the pen-shaped main body 101, so as to enhance acoustic coupling between the sensor module 211 and a human being. The top of bell module 137 contains a housing designed to attach bell module 137 to the bottom of pen-shaped main body 101 contiguous with exterior housing 131. Bell module 137 attaches at the same position where protective cap 113 attaches to stethoscope 101 and cannot be attached when cap 113 is attached. Bell module 137 exterior housing includes a tab on the back side that is disposed contiguous with the back side of stethoscope 101 when bell module 137 is attached. This tab facilitates removal of bell module 137 from stethoscope 101. The bottom of bell module 137 includes a bell frame 139 and a ring holder 140 that secures vibration film 138 in position. The bell frame 139 surrounds the ring holder 140. Use of the bell module provides enhanced acoustic coupling with the skin of a patient during auscultation for a stronger audio signal in some frequency ranges of clinical interest.

Figure 1I:
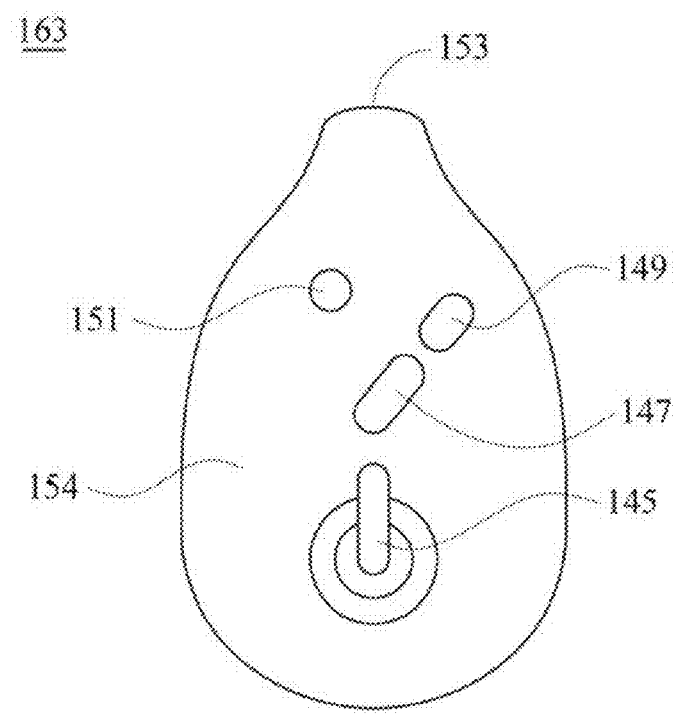
FIG. 1I is a front orthogonal view of a wireless receiver showing several external user interface controls of the wireless receiver control module according to one embodiment of the present disclosure.
Figure 1J:
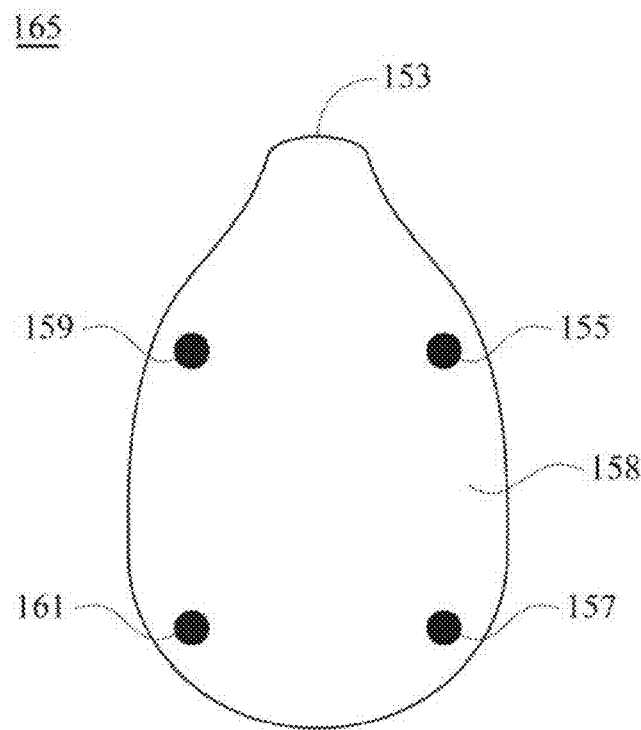
FIG. 1J is a back orthogonal view of the wireless receiver of FIG. 1I.
Figure 1K:
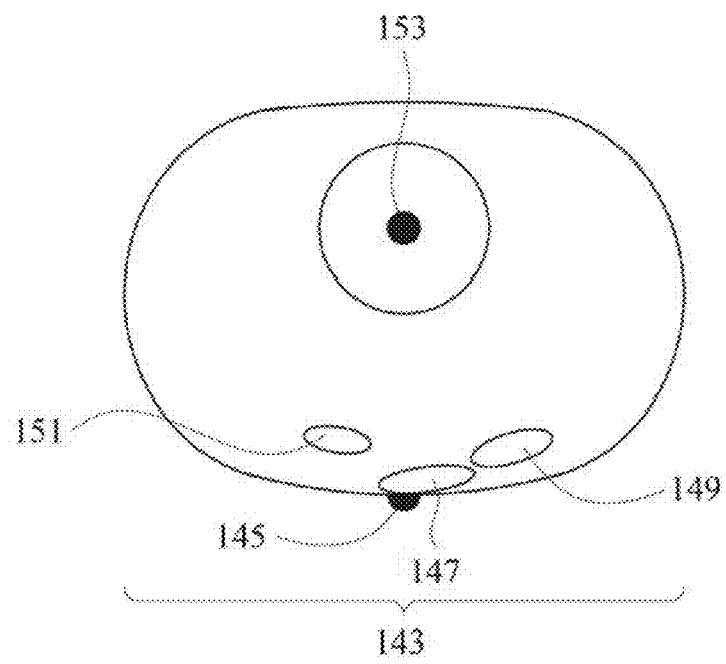
FIG. 1K is a top orthogonal view of the wireless receiver of FIG. 1I showing the external audio jack of the wireless receiver audio module.

FIGS. 1I through 1K illustrate the wireless receiver. FIG. 1I shows an orthogonal view of the front of wireless receiver 143, which includes four user interface controls of the wireless receiver control module. These include power switch 145 that physically enables and disables transfer of electrical energy from the wireless receiver power module to other modules. In addition, buttons 147 and 149 increase and decrease, respectively, the signal strength of output from the wireless receiver audio module via audio output port, or jack, 153, which accepts a standard 3.5 millimeter "mini" stereo audio plug for output transmission of electrical audio signals. The audio output jack 153 is located on a side of the receiver body 202 for receiving an audio plug. The button 151 establishes connection between the wireless communication module of wireless receiver 143 and the main body wireless communication module of stethoscope 101. The front exterior case 163 shown in FIG. 1I and the back exterior case 165 shown in FIG. 1J are contiguous aligning along their perimeter edges clamshell-style sandwiching the internal components of the wireless receiver. Retaining screws 155, 157, 159, and 161 secure cases 163 and 165 together maintaining the alignment of perimeter edges. Cases 163 and 165 are designed to have smooth external contours for comfort of the user, especially while the wireless receiver is not in use and is stored in a pocket or resting on the user's chest in the style of a pendant at the end of a necklace. FIG. 1K shows a top view of wireless receiver 143. The exterior audio port 153 is visible, as are perspective views of four user interface controls 145, 147, 149, and 151.

Functional Component Modules of the Wireless Electronic Stethoscope

Figure 2A:
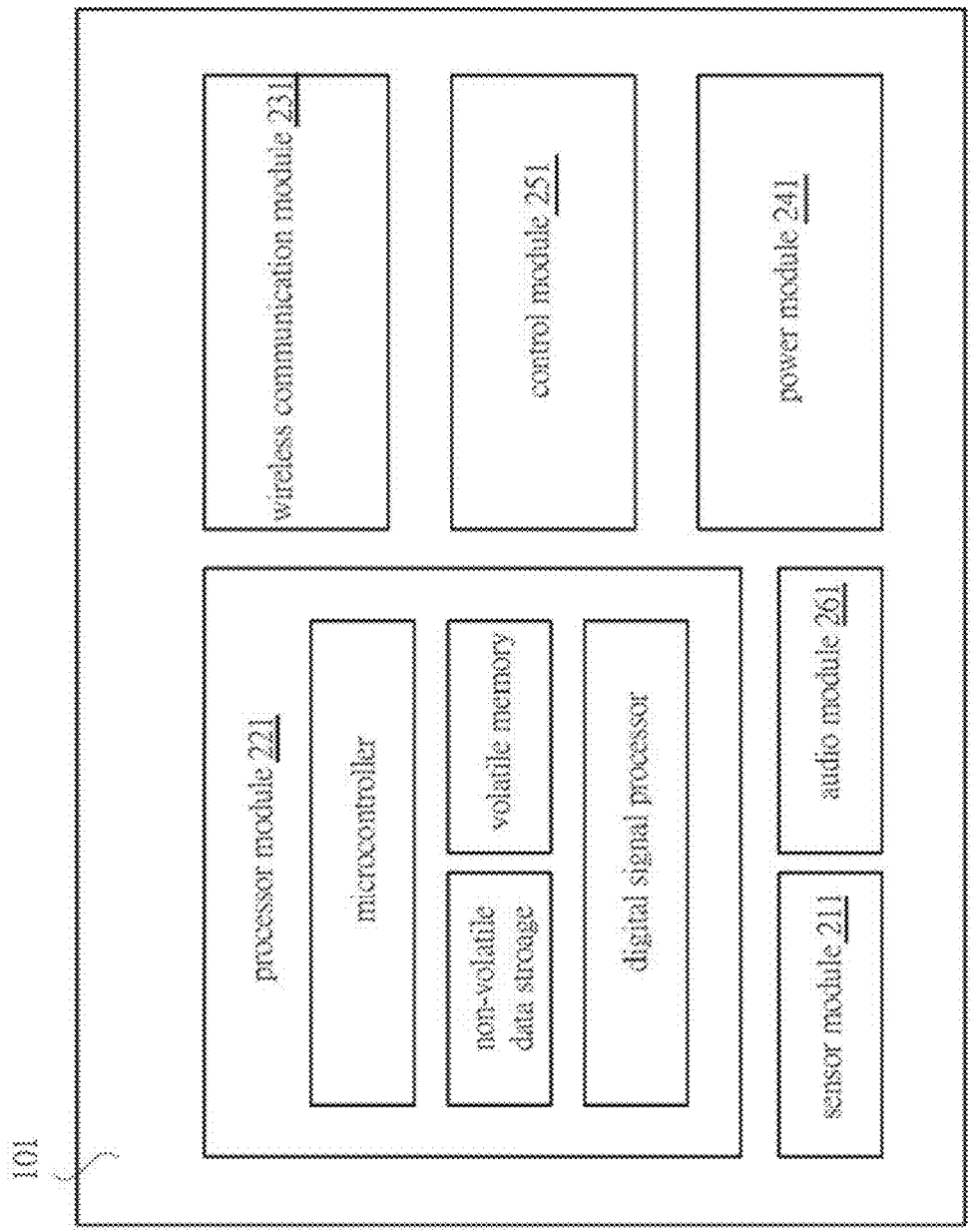
FIG. 2A is an electronic block diagram illustrating components of a wireless electronic stethoscope according to one embodiment of the present disclosure.

The design of the underlying electronic architecture can be represented in terms of the constituent functional component modules, which, together, provide the functionality presented to a user. FIG. 2A contains an electronic block diagram indicating the functional component modules of the wireless electronic stethoscope main body. Structurally, the sensor module 211, the processor module 221, the wireless communication module 231, the power module 241, the control module 251 and the audio module 261 are located in the pen-shaped main body 101. The sensor module 211 can sense an audio signal from a human being; for example, the sensor module 211 may be a contact microphone, piezoelectric microphone, micro-electrical mechanical system microphone, electromagnetic microphone, or semiconductor process microphone. The processor module 221 can filter the audio signal to retain audio data in a predetermined frequency range. The wireless communication module 231 can wirelessly transmit the audio data. The control module 251 is exposed to a side of the pen-shaped main body and configured to receive operational commands that include a command of adjusting the predetermined frequency range. The audio module 261 can transmit the audio signal to the audio output jack 153.

The processor module 221 contains a micro-controller or other central processing unit that runs embedded computer software to coordinate the operation of the wireless stethoscope component modules. Volatile memory, such as random access memory (RAM), holds the value of current running program state information, which is lost when the flow of electrical energy from the power module 241 is stopped. Non-volatile storage, such as flash memory or other electrically erasable programmable read-only memory (EEPROM), holds computer programming code and device configuration files installed during manufacturing that persist after the flow of electrical energy from the Power Module is stopped. Moreover, this non-volatile storage may be used to store digital audio files created from patient body sounds that are captured by the sensor module at the bottom of pen-shaped main body 101. A digital signal processor provides frequency range filtering of digital audio signal such as low-pass filtering, high-pass filtering, and band-pass filtering. These, and additional digital signal processing algorithms can optimize the audio signal that is presented to a clinician by processing to highlight those frequencies that are of greatest clinical relevance when diagnosing a particular patient. The non-volatile data storage, volatile memory, and even digital signal processing capability may be physically present in separate integrated circuit packages on an electronic printed circuit board within the wireless stethoscope main body. Alternatively, some, or all, of the components of the processor module may be combined within a single integrated circuit package. This varies depending on current product offerings from suppliers and may change with prevailing technology and electronic component market conditions.

The sensor module 211 includes the microphone and the electronics to power and support the operation of the microphone. The choice of microphone and the supporting electronics may also vary depending on current product offerings from suppliers and electronic component market conditions. For example, use of a contact microphone may require filtering of audio signals to reduce noise generated by abrasive shear forces applied to the thin film material during contact with the patient's body. If a capacitive microphone is used, the thickness of the bell diaphragm must be selected to provide an adequate audio signal for the frequency ranges of clinical interest Processing of the audio signal generated by the sensor module 211 is provided by the digital signal processor of the processor module 221 to highlight particular frequency ranges of interest to the clinician. For example, 200-10,000 hertz audio frequencies are clinically relevant for the diagnosis of many respiratory conditions. In contrast, 30-80 hertz audio frequencies are clinically relevant to diagnosis of mitral stenosis, a heart condition. The wireless electronic stethoscope has three modes of operation regarding the processing of audio signals. "Bell Mode" amplifies the 20-1,000 hertz range while emphasizing frequencies in the 20-200 hertz range. "Diaphragm Mode" amplifies the 20-2,000 hertz range while emphasizing frequencies in the 100-500 hertz range. "Extend Mode" amplifies the 20-20,000 hertz range while emphasizing frequencies in the 50-500 hertz range. The clinician may select an appropriate mode using user interface control button 135 shown in FIG. 1G.

The audio module 261 delivers live audio signals received from the microphone of the sensor module, or previously-recorded audio data files stored in the non-volatile storage of the processor module, to audio output jack 128 shown in FIG. 1C. The audio output jack 128 is located on a side of the pen-shaped main body 101 for receiving a audio plug. This provides the user access to audio data via speakers or headphones plugged into output jack 128 without relying upon wireless transmission of the data to wireless receiver 143 shown in FIG. 1I. Buttons 107 and 109 shown in FIG. 1A control the volume of the audio signal delivered to the user.

The power module 241 manages the delivery of power to all other modules. It includes a battery and voltage regulators to provide 3.3 volt and 5.0 volt direct electric current to module components as necessary. Advanced power management circuitry can communicate with the processor module, for notification of the user about battery energy levels, and emergency shut-off if energy levels become too low to maintain a sufficient output current and voltage level to support the other modules.

The control module 251 includes all the user interface controls visible on the exterior of wireless stethoscope 101 and the supporting internal electric circuitry. These controls include buttons switches, indicator lights, and a display screen.

The wireless communication module 231 supports a wireless communication protocol. This may be a peer-to-peer personal area network protocol such as Bluetooth or electronic networking protocols such as Internet. Protocol (IP), Transmission Control Protocol (TCP), or User Datagram Protocol (UDP). The wireless communication module includes the necessary protocol stack software, radio frequency circuitry, and antenna. The wireless communication module 231 provides data links with one or more receiver modules.

Figure 2B:
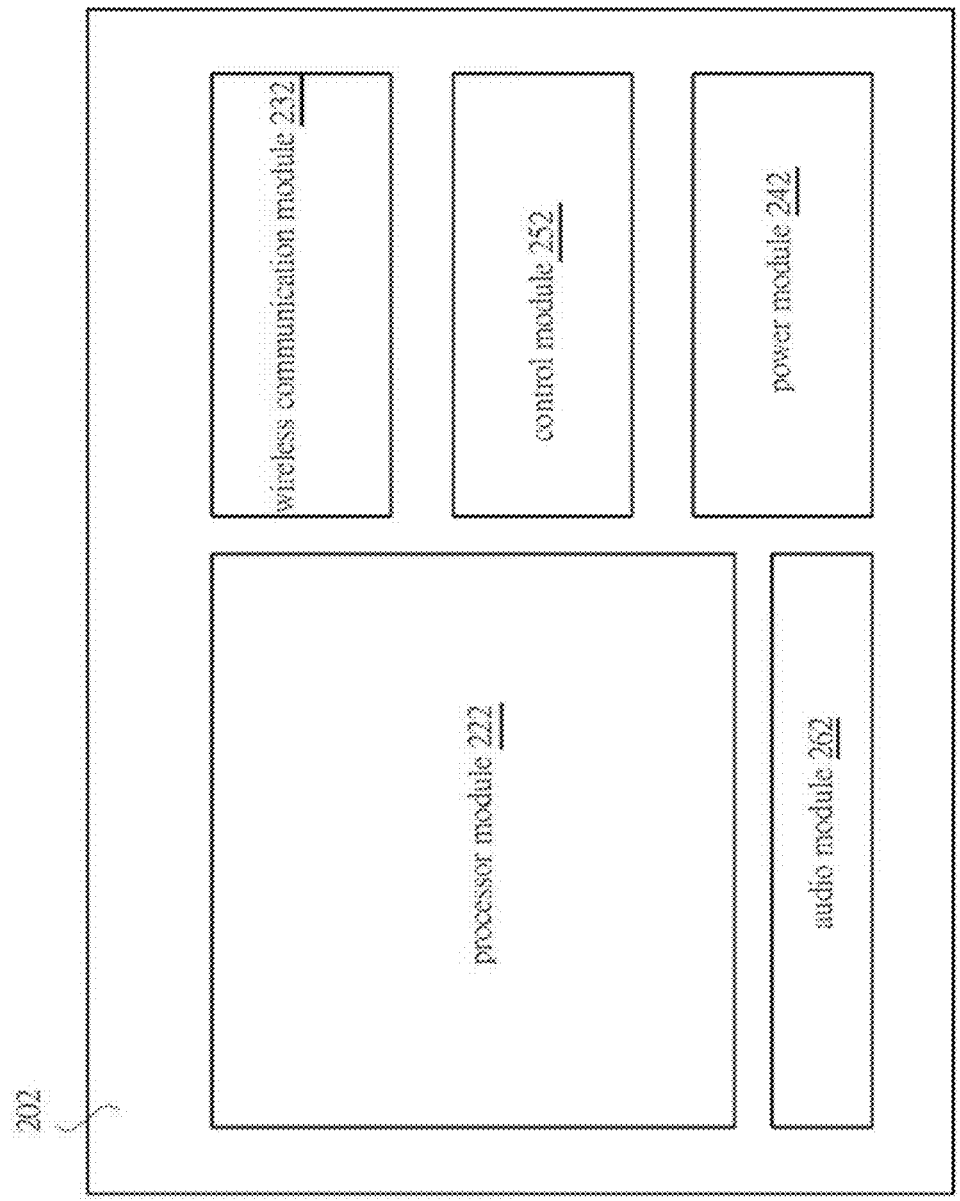
FIG. 2B is an electronic block diagram illustrating components of a wireless receiver according to one embodiment of the present disclosure.

FIG. 2B contains an electronic block diagram indicating the functional component modules of the wireless receiver. The wireless receiver configured to receive the audio data from the wireless communication module 231 of the pen-shaped main body 101. Structurally, the processor module 222, the wireless communication module 232, the power module 242, the control module 252 and the audio module 262 are located in the receiver body 202. The power module 242, the wireless communication module 232, and the control module 252 function in a manner similar to the corresponding modules of the stethoscope main body. The wireless receiver does not contain a sensor module. The wireless communication module 232 is configured to wirelessly receive the audio data. The audio module 262 transmits the audio signal to the audio output jack 153.

The wireless receiver audio module 262 is similar to the main body audio module 261, except for the source of audio data. It does not have access to live audio signals from the microphone in the main body sensor module or previously-recorded audio data files in a processor module. Instead, the source of audio signals is the wireless receiver wireless communication module, which receives audio data from the stethoscope main body wireless communication module.

Finally, the wireless receiver processor module coordinates the operation of all modules in the wireless receiver. However, unlike the processor module of the stethoscope main body, it does not perform advanced digital signal processing and it does not provide non-volatile data storage for recorded audio data files.

Power Saving Mode

Figure 3:
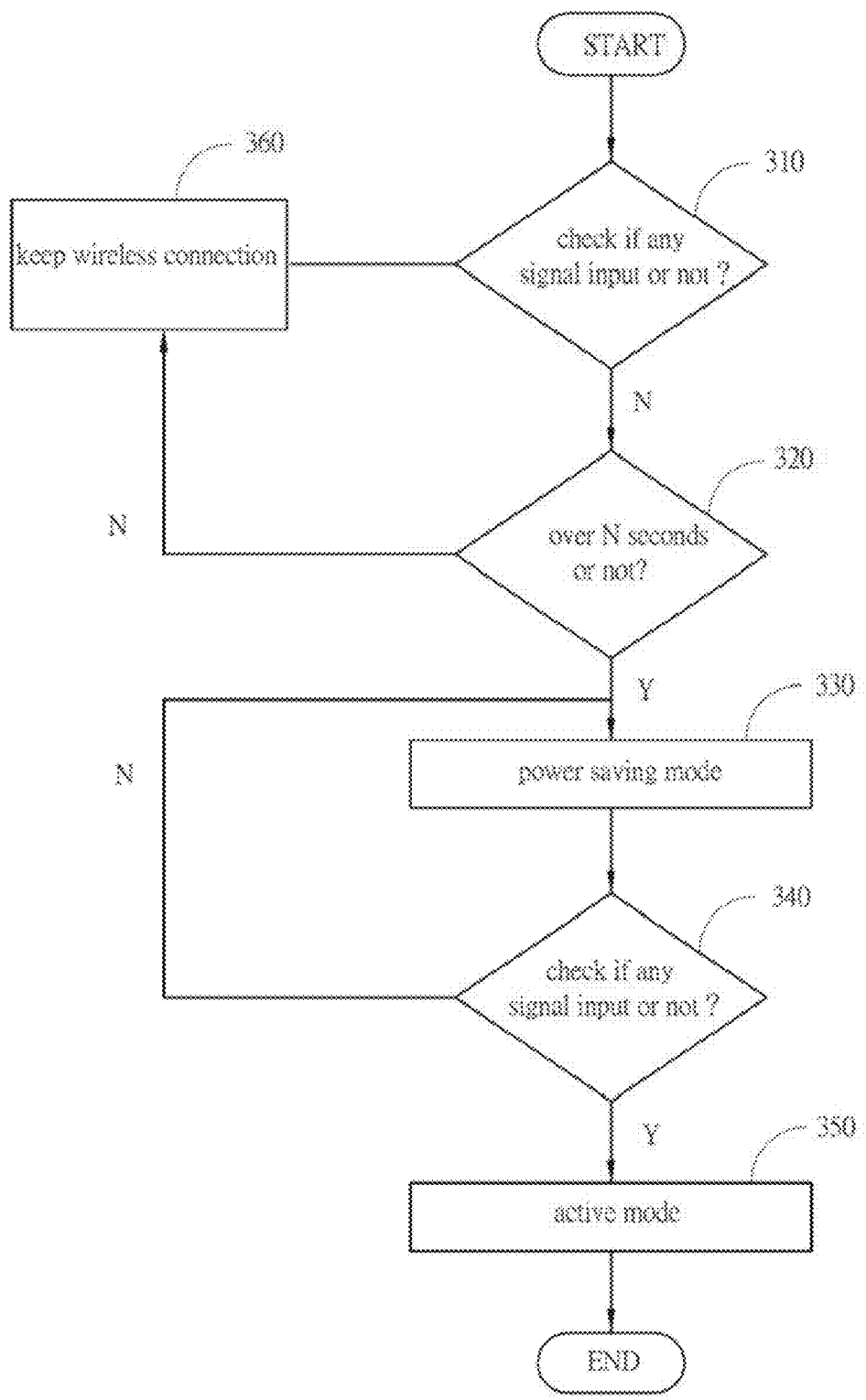
FIG. 3 is a flowchart illustrating operational logic of the power saving mode of a wireless electronic stethoscope according to one embodiment of the present disclosure.

An embodiment of this invention includes a Power Saving Mode design. As shown in FIG. 3, the main function of the Power Saving Mode is to conserve power. Because the wireless module transmission requires high power consumption, power management is an important aspect of the pen-shaped wireless stethoscope. The operational flow of the Power Saving Mode is designed as follow. The system will automatically detect the state of the Sensor Module. In step 310, upon receiving an incoming signal, the Wireless Communication Module will leave the power saving mode and will automatically connect with the Wireless Receiver Module in step 360. After a lapsed of N seconds without receiving any signal in step 320, the First Wireless Communication Module and the Wireless Receiver will automatically enter a power saving mode in step 330. In step 340, upon receiving an incoming signal, the Wireless Receiver will automatically enter an active mode.

Single Button Control

Figure 4:
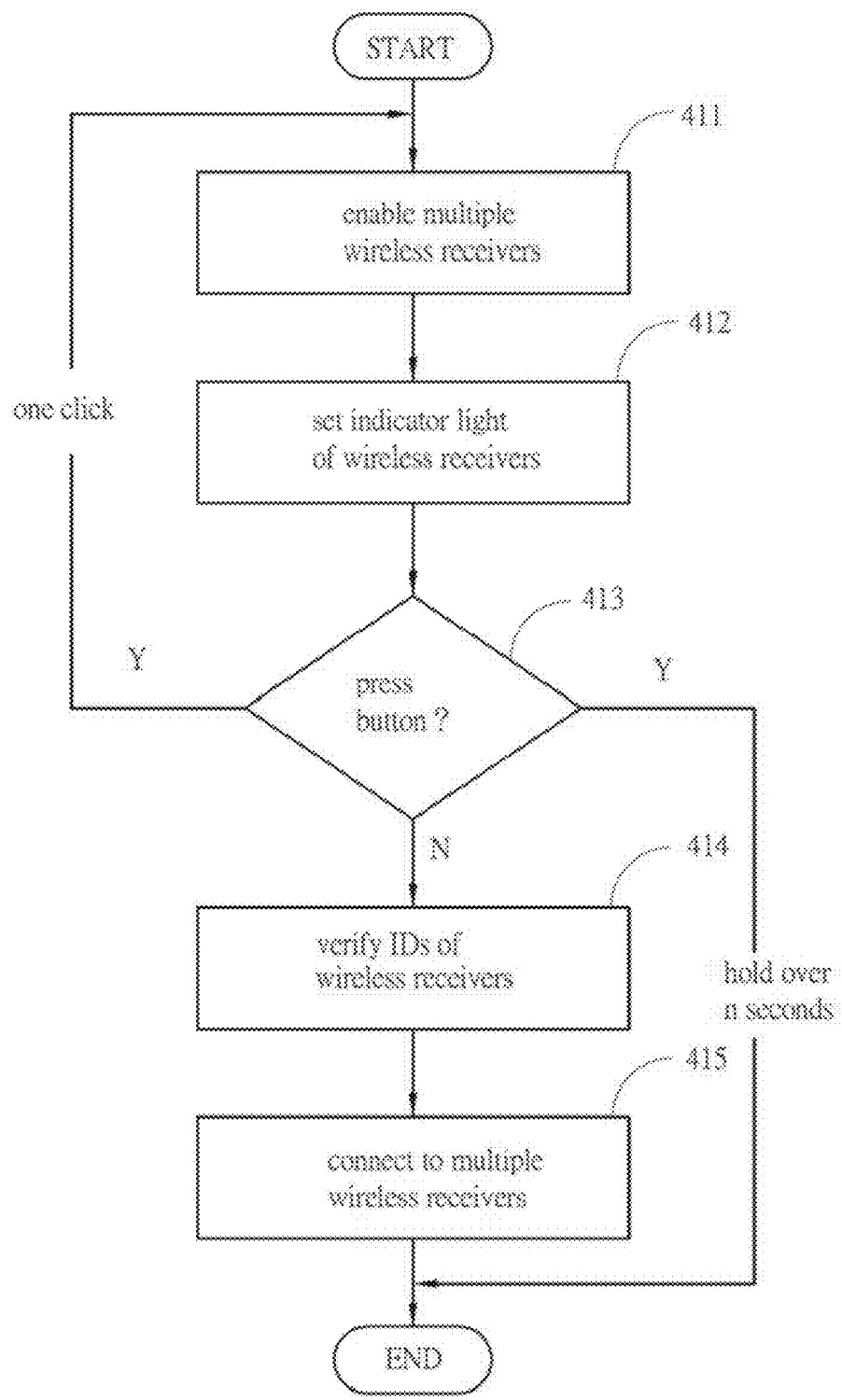
FIG. 4 is a flowchart illustrating operational logic of the coordination of communication between the electronic stethoscope main body and multiple wireless receivers according to one embodiment of the present disclosure.
Figure 5:
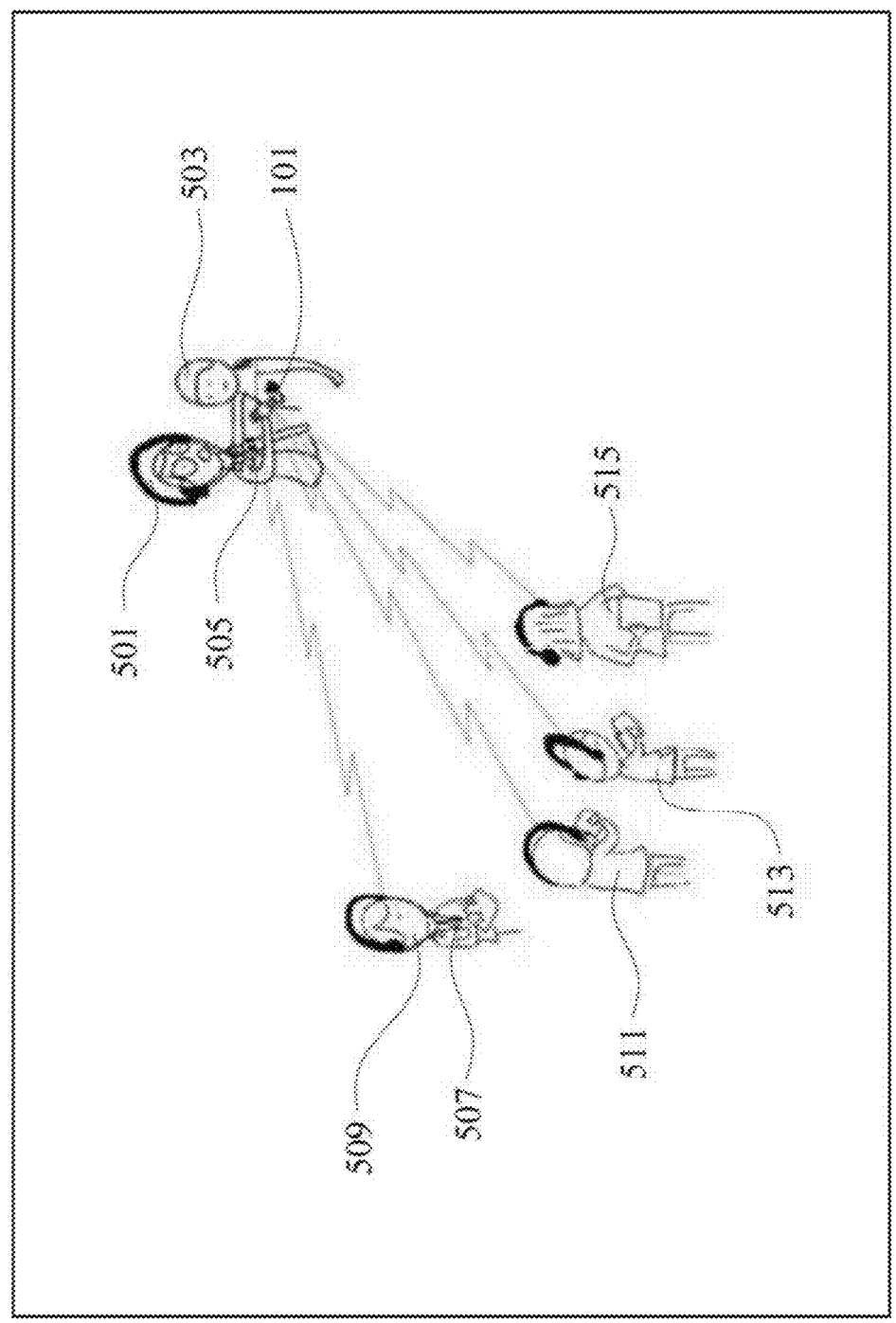
FIG. 5 is illustration of the use of a wireless electronic stethoscope to transfer clinical data to multiple wireless receivers according to one embodiment of the present disclosure.

In one embodiment, Single Button Control is included, through Control Button 135 in FIG. 1G. In one embodiment, a single button (e.g., button 135) is located on a side of the pen-shaped main body and configured to wirelessly transmit the audio data to the wireless receiver when pressed. Single Button Control can be used to control the plurality of wireless receivers. FIG. 4 shows the control flow for the plurality of wireless receivers. We can decide which device works as the master that allows other receivers to connect. First, wireless receivers are enabled in step 411, and then indicator lights of these wireless receivers can be set in step 412. In step 413, it is determined whether a control button (signal button) is pressed. When the control button is pressed, the IDs of the wireless receivers are verified in step 414 and then the electronic stethoscope device is connected to the wireless receivers. For example as illustrated in FIG. 5, a professor 501 examines a patient 503 using the wireless electronic stethoscope 101 with 4 students 509, 511, 513 and 515. As he finds an abnormal heart sound he would like his students to listen at the same time. For this situation, he can set his electronic stethoscope 101 to "master mode" and his students stethoscope set to "slave mode" to share the body sound. Later, he can also assign a student 509 using a wireless receiver 507 to operate in the master mode and operate and explain what he hears.

The Control Button 135 also can be used as Multiple Function control button in the future. In one embodiment, power, volume, mode selection, record and play/pause buttons can be controlled by a signal button and touch screen panel to create a user-friendly interface.

Electronic Network Data Communication Protocol

Figure 6:
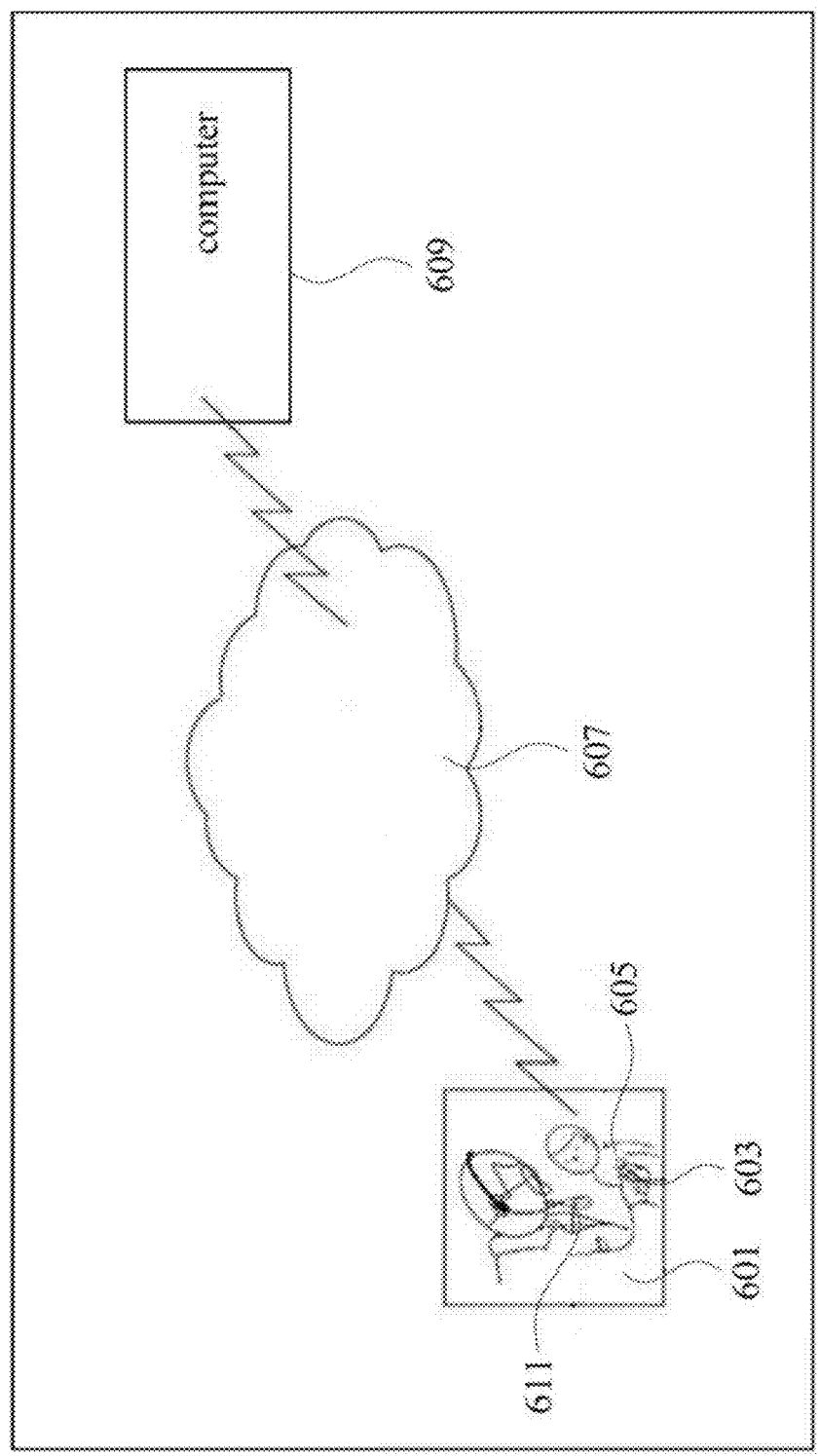
FIG. 6 is illustration of the use of a wireless electronic stethoscope to transfer clinical data to a computer via an electronic data network according to one embodiment of the present disclosure.

In one embodiment, the wireless electronic stethoscope is used with an electronic network data communication protocol. FIG. 6 shoves a wireless electronic stethoscope 603 can transmit data to an electronic data network 607 at the same time when Doctor 601 uses a wireless electronic stethoscope 603 to diagnose patient 605. Computer 609 performs computational analysis of data received from electronic network data communication protocol. Alternatively, this can be done via cloud computing.

Figure 7:
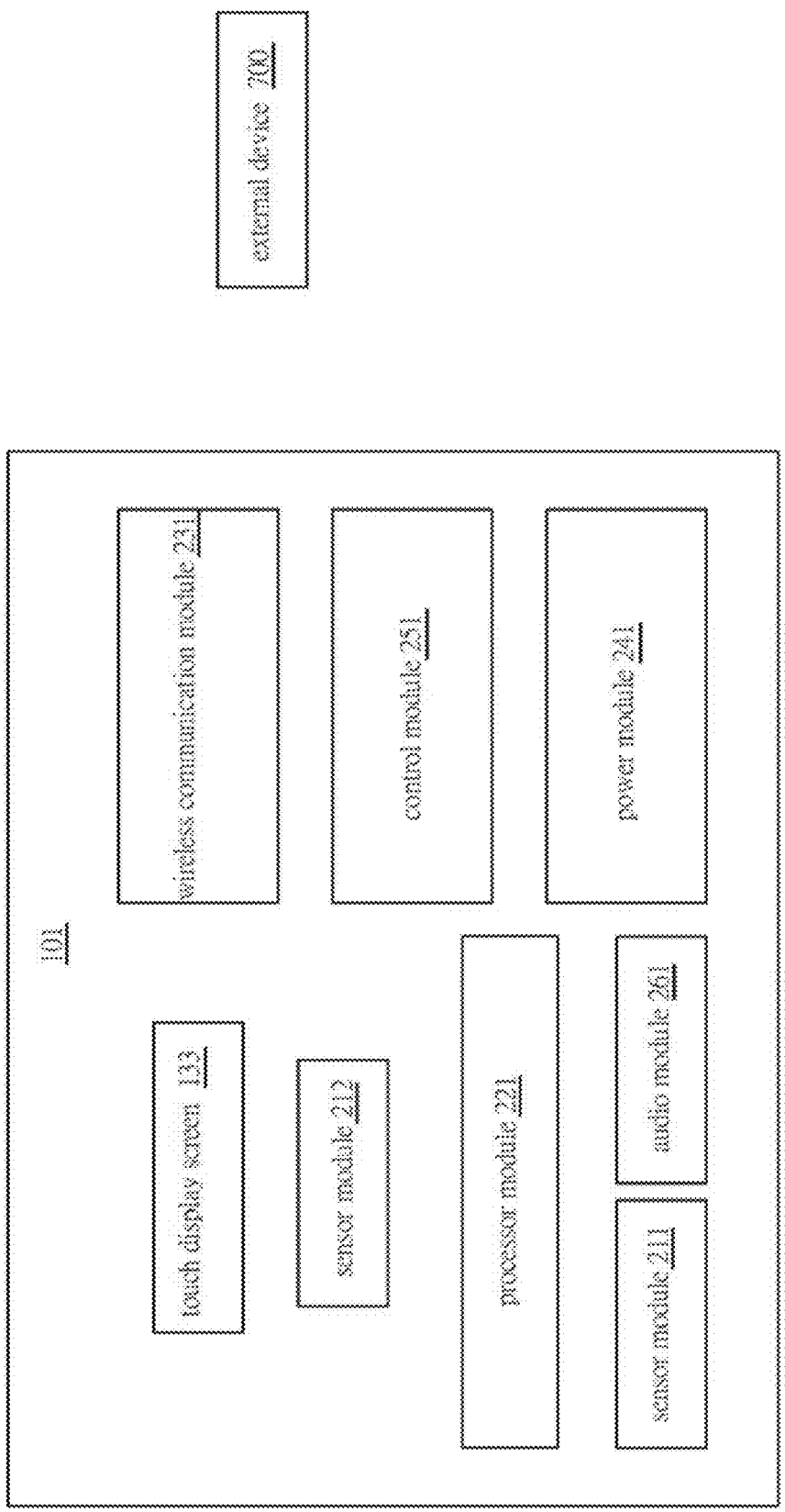
FIG. 7 is an electronic block diagram illustrating components of an electronic stethoscope device according to one embodiment of the present disclosure.

FIG. 7 is an electronic block diagram illustrating components of an electronic stethoscope device according to one embodiment of the present disclosure. As shown in FIG. 7, the electronic stethoscope device includes the touch display screen 133, the sensor module 211, 212, the processor module 221, the wireless communication module 231, the power module 241, control module 251 and the audio module 261. The external device 700 may be a computer, a mobile device, servers (e.g., cloud server or hospital server), or the combination thereof.

The wireless communication module 231 of the pen-shaped main body 101 wirelessly transmits the audio data to a computer or a mobile device, and the computer or the mobile device supports communication via above electronic network data communication protocol. The computer or the mobile device performs computational analysis of audio data received from the wireless communication module 231 of the pen-shaped main body 101 via the electronic network data communication protocol.

The wireless communication module 231 of the pen-shaped main body 101 is wirelessly connected to a computer or a mobile device, the computer or the mobile device is synchronized with the electronic stethoscope device; the computer or the mobile device transmits information to the electronic stethoscope device, or the electronic stethoscope device transmits information to the computer or the mobile device; the computer or the mobile device transmits data to a cloud server or a hospital server.

The sensor module 212 (e.g. an accelerometer, an electronic gyroscope, or a piezoelectric film sensor) is located in the pen-shaped main body 101, and configured to detect an activity signal, breathing and sleep states, and heartbeat frequency of the human being, wherein the processor module 221 is configured to filter and amplify the activity signal, the breathing and sleep states, and the heartbeat frequency to get a physiological signal.

When the processor module 221 determines that the physiological signal is abnormal, a touch display screen 133 of the electronic stethoscope device or a message and a SMS (short message service) notification of the computer and the mobile device shows an abnormal status.

In view of all of the above and the Figures, it should be readily apparent to those skilled in the art that the present disclosure introduces a wireless electronic stethoscope device comprises: a pen-shaped main body, a sensor module for data collection, a processor module to coordinate operation of electronic stethoscope modules, a wireless communication module to transmit and receive digital and analog data, a power module including a battery for storing energy; and a control module to communicate information and receive operational commands. The sensor module includes a contact microphone, piezoelectric microphone, micro-electrical mechanical system microphone, electromagnetic microphone, or semiconductor process microphone. The processor module performs analog to digital electrical signal conversion, frequency range electrical signal filtering, or other digital signal processing operations on data provided by said sensor module. The control module comprises a plurality of buttons, switches, indicator lights, or other control interfaces. The control module includes a touch-sensitive display screen that also functions as a control mechanism to receive operational commands. The pen-shaped main body has an exterior clip. The control module includes an indicator which communicates to a user whether a current position of said sensor module on a patient's body is sufficient to enable communication of an adequate data signal from said sensor module. The power module has a power saving mode of operation. The wireless electronic stethoscope device further comprises a detachable bell module, which, upon attachment to said main body, is disposed contiguous with said sensor module. The wireless electronic stethoscope device further comprises an audio module that transmits an audio signal to an electronic audio output jack. The wireless electronic stethoscope device further comprises a wireless receiver comprising: a processor module to coordinate operation of the wireless receiver modules; a wireless communication module to transmit data to, and receive data from, the wireless communication module of the pen-shaped main body; a power module including a battery for storing energy; a control module to communicate information and receive operational commands; and an audio module that transmits an audio signal to an electronic speaker or to an electronic audio output jack. The communication module of the pen-shaped main body can transmit and receive data to a plurality of wireless receivers. The control module of the pen-shaped main body enables the transmission of data to said plurality of wireless receivers using a single button. The wireless communication module of the pen-shaped main body supports an electronic network data communication protocol. The wireless electronic stethoscope device further comprises a computer supporting communication via said electronic network data communication protocol. The computer performs computational analysis of data received from said wireless communication module of the pen-shaped main body via said electronic network data communication protocol.

The present disclosure also introduces a method of detecting and transmitting body sounds wirelessly, comprising the steps of: detecting body sounds through a detached wireless electronic stethoscope; and transmitting said body sounds simultaneously to one or more receivers, wherein said body sounds can be stored and retrieved by one or more receivers; or said body sounds can be analyzed for screening or diagnostic purposes. Said screening or diagnosis is conducted in a separate location from said detached wireless electronic stethoscope. Said screening or diagnosis is conducted through the use of cloud computing.

The present disclosure yet also introduces a method of detecting and transmitting body sounds wirelessly, comprising the steps of: detecting body sounds through a detached wireless electronic stethoscope; and transmitting said body sounds simultaneously to one or more mobile computing devices. Said body sounds can be stored and retrieved by one or more desktop or mobile computing devices; or said body sounds can be analyzed for screening or diagnostic purposes. Said screening or diagnosis is conducted in a separate location from said detached wireless electronic stethoscope. Said screening or diagnosis is conducted through the use of cloud computing. Said screening or diagnosis is performed by an automated expert system. Said screening or diagnosis is performed for population-level analysis.

The foregoing description has been presented for purposes of illustration and description. It is not intended to be exhaustive or to limit the invention to the precise forms disclosed. Obvious modifications or variations are possible in light of the above teachings. The embodiment or embodiments discussed were chosen and described to provide the best illustration of the principles of the invention and its practical application to thereby enable one of ordinary skill in the art to utilize the invention in various embodiments and with various modifications as are suited to the particular use contemplated.

All such modifications and variations are within the scope of the invention as determined by the appended claims when interpreted in accordance with the breadth to which they are fairly and legally entitled.

What is claimed is:

1. A wireless electronic stethoscope device, comprising:
   a pen-shaped main body;
   a sensor module for data collection;
   a processor module to coordinate operation of electronic stethoscope modules;
   a wireless communication module to transmit and receive digital and analog data;
   a power module including a battery for storing energy; and
   a control module to communicate information and receive operational commands,
   wherein said control module includes an indicator which communicates to a user whether a current position of said sensor module on a patient's body is sufficient to enable communication of an adequate data signal from said sensor module.

2. The wireless electronic stethoscope device of claim 1, wherein said sensor module includes a contact microphone, piezoelectric microphone, micro-electrical mechanical system microphone, electromagnetic microphone, or semiconductor process microphone.

3. The wireless electronic stethoscope device of claim 1, wherein said processor module performs analog to digital electrical signal conversion, frequency range electrical signal filtering, or other digital signal processing operations on data provided by said sensor module.

4. The wireless electronic stethoscope device of claim 1, wherein said control module comprises a plurality of buttons, switches, indicator lights, or other control interfaces.

5. The wireless electronic stethoscope device of claim 1, wherein said control module includes a touch-sensitive display screen that also functions as a control mechanism to receive operational commands.

6. The wireless electronic stethoscope device of claim 1, further comprising:
   a detachable bell module, which, upon attachment to said main body, is disposed contiguous with said sensor module.

7. The wireless electronic stethoscope device of claim 1, further comprising:
   a wireless receiver, comprising:
   a processor module to coordinate operation of the wireless receiver modules;
   a wireless communication module to transmit data to, and receive data from, the wireless communication module of the pen-shaped main body;
   a power module including a battery for storing energy;
   a control module to communicate information and receive operational commands; and
   an audio module that transmits an audio signal to an electronic speaker or to an electronic audio output jack.

8. The wireless electronic stethoscope device of claim 7, wherein said communication module of the pen-shaped main body can transmit and receive data to a plurality of wireless receivers.

9. The wireless electronic stethoscope device of claim 8, wherein said control module of the pen-shaped main body enables the transmission of data to said plurality of wireless receivers using a single button.

10. The wireless electronic stethoscope device of claim 1, wherein said wireless communication module of the pen-shaped main body supports an electronic network data communication protocol.

11. The wireless electronic stethoscope device of claim 10, further comprising a computer supporting communication via said electronic network data communication protocol.

12. The wireless electronic stethoscope device of claim 11, wherein said computer performs computational analysis of data received from said wireless communication module of the pen-shaped main body via said electronic network data communication protocol.

13. The wireless electronic stethoscope device of claim 4, wherein:
   the plurality of buttons includes a plurality of audio frequency buttons, each audio frequency button enabling amplification of a predetermined frequency range, and
   the predetermined frequency ranges associated with the plurality audio frequency buttons are different from one another.

14. The wireless electronic stethoscope device of claim 4, wherein:
   the plurality of buttons includes a master button that is configured to set the wireless electronic stethoscope as a master device, and
   the master device transmits the digital and analog data to another wireless electronic stethoscope device.

15. The wireless electronic stethoscope device of claim 1, wherein:
   upon the sensor module detecting a physiological anomaly, the processor module generates a health report indicating the physiological anomaly and transmits the health report to a receiver, and
   the health report comprises at least one selected from a group consisting of: a heart rate and a respiratory rate.

16. A method of detecting and transmitting body sounds wirelessly, comprising the steps of:
   determining that a current position of a detached wireless electronic stethoscope on a patient's body is sufficient to enable communication of an adequate data signal from said the detached wireless electronic stethoscope;
   detecting body sounds through the detached wireless electronic stethoscope; and
   transmitting said body sounds simultaneously to one or more receivers, wherein:
   said body sounds can be stored and retrieved by one or more receivers; or
   said body sounds can be analyzed for screening or diagnostic purposes.

17. The method of claim 16, wherein:
   said screening or diagnosis is conducted in a separate location from said detached wireless electronic stethoscope.

18. The method of claim 17, wherein:
   said screening or diagnosis is conducted through the use of cloud computing.

19. A method of detecting and transmitting body sounds wirelessly, comprising the steps of:
   determining that a current position of the detached wireless electronic stethoscope on a patient's body is sufficient to enable communication of an adequate data signal from the detached wireless electronic stethoscope;
   detecting body sounds through the detached wireless electronic stethoscope; and
   transmitting said body sounds simultaneously to one or more mobile computing devices.

20. The method of claim 19, wherein:
   said body sounds can be stored and retrieved by one or more desktop or mobile computing devices; or
   said body sounds can be analyzed for screening or diagnostic purposes.

21. The method of claim 20, wherein:
said screening or diagnosis is conducted in a separate location from said detached wireless electronic stethoscope.

22. The method of claim 21, wherein:
said screening or diagnosis is conducted through the use of cloud computing.

23. The method of claim 20, wherein:
said screening or diagnosis is performed by an automated expert-system.

24. The method of claim 20 wherein:
said screening or diagnosis is performed for population-level analysis.

25. A system comprising:
a master wireless electronic stethoscope; and
a plurality of slave wireless electronic stethoscopes,
wherein the master wireless electronic stethoscope is configured to detect a physiological sign of a patient and transmit the physiological sign to each of the plurality of slave wireless electronic stethoscopes,
wherein each of the plurality of slave wireless electronic stethoscopes is configured to store and playback the physiological sign, and
wherein the physiological sign is at least one selected from a group consisting of: respiratory rate and heart rate.

* * * * *